(12) United States Patent
Yee et al.

(10) Patent No.: US 8,016,420 B2
(45) Date of Patent: Sep. 13, 2011

(54) SYSTEM AND METHOD FOR ILLUMINATION AND FIXATION WITH OPHTHALMIC DIAGNOSTIC INSTRUMENTS

(75) Inventors: Kingman Yee, San Jose, CA (US); Seema Somani, Milpitas, CA (US)

(73) Assignee: AMO Development LLC., Santa Ana, CA (US)

( * ) Notice: Subject to any disclaimer, the term of this patent is extended or adjusted under 35 U.S.C. 154(b) by 32 days.

(21) Appl. No.: 11/750,291

(22) Filed: May 17, 2007

(65) Prior Publication Data

US 2008/0284979 A1    Nov. 20, 2008

(51) Int. Cl.
*A61B 3/10* (2006.01)
(52) U.S. Cl. ....................................................... 351/211
(58) Field of Classification Search ............ 351/209–211
See application file for complete search history.

(56) References Cited

U.S. PATENT DOCUMENTS

| | | |
|---|---|---|
| 4,190,332 A | 2/1980 | Body et al. |
| 4,702,596 A | 10/1987 | Nohda |
| 4,778,268 A | 10/1988 | Randle |
| 5,483,305 A | 1/1996 | Kohayakawa |
| 5,555,039 A | 9/1996 | Iki et al. |
| 6,004,313 A | 12/1999 | Shimmick et al. |
| 6,052,180 A | 4/2000 | Neal et al. |
| 6,059,773 A | 5/2000 | Maloney et al. |
| 6,095,651 A | 8/2000 | Williams et al. |
| 6,120,149 A | 9/2000 | Hosoi |
| 6,271,915 B1 | 8/2001 | Frey et al. |
| 6,280,435 B1 | 8/2001 | Odrich et al. |
| 6,550,917 B1 | 4/2003 | Neal et al. |
| 6,598,975 B2 | 7/2003 | Liang et al. |
| 6,634,750 B2 | 10/2003 | Neal et al. |
| 6,655,805 B2 | 12/2003 | Fujieda |
| 6,932,808 B2 | 8/2005 | Gross |
| 7,261,412 B2 | 8/2007 | Somani et al. |
| 7,293,873 B2 | 11/2007 | Dai et al. |
| 2004/0061830 A1 | 4/2004 | Hellmuth et al. |
| 2004/0218142 A1 | 11/2004 | Wakil et al. |

(Continued)

FOREIGN PATENT DOCUMENTS

EP    1138252    10/2001

(Continued)

OTHER PUBLICATIONS

Leibowitz et al., "New Evidence for the Intermediate Position of Relaxed Accomodation," Documenta Ophthalmologica, Oct. 16, 1978;46(1):133-47.

(Continued)

*Primary Examiner* — Ricky L Mack
*Assistant Examiner* — Mahidere S Sahle

(57) ABSTRACT

An eye measurement system may include a target that moves transverse to an optical path from the target to eye, so as to relax accommodation of the lens of the eye. The target may move transverse to the optical path on a display. The patient may be fogged while the target moves transverse to the optical path, and the target may become smaller such that the patient perceives the target to be moving away from the patient. A pupil camera may measure eye position that can be correlated with the position of the target on the display to determine that the patient has maintained fixation on the moving target. A visible measurement light beam may be pulsed subsequent to and/or during motion of the target that relaxes accommodation of the eye so as to avoid visual interference of the measurement light beam with the target on the display.

23 Claims, 8 Drawing Sheets

U.S. PATENT DOCUMENTS

| | | |
|---|---|---|
| 2005/0041210 A1 | 2/2005 | Isogai et al. |
| 2005/0110948 A1 | 5/2005 | Bille |
| 2005/0124983 A1 | 6/2005 | Frey et al. |
| 2005/0146685 A1 | 7/2005 | Hanaki et al. |
| 2005/0174535 A1 | 8/2005 | Lai et al. |
| 2005/0203422 A1 | 9/2005 | Wei |
| 2005/0261752 A1 | 11/2005 | Chernyak |
| 2005/0270491 A1 | 12/2005 | Dai et al. |
| 2005/0280777 A1 | 12/2005 | Dai |
| 2006/0017883 A1 | 1/2006 | Dai et al. |
| 2006/0023161 A1 | 2/2006 | Imaizumi |
| 2006/0061731 A1 | 3/2006 | Kuhn et al. |
| 2006/0087618 A1* | 4/2006 | Smart et al. .................. 351/222 |
| 2006/0244911 A1* | 11/2006 | Shimizu et al. ............... 351/202 |
| 2006/0264916 A1 | 11/2006 | Yee |
| 2007/0177104 A1 | 8/2007 | Lacombe et al. |
| 2007/0236659 A1* | 10/2007 | Yamaguchi et al. .......... 351/205 |

FOREIGN PATENT DOCUMENTS

| | | |
|---|---|---|
| EP | 1452126 | 9/2004 |
| GB | 2359375 A * | 8/2001 |

OTHER PUBLICATIONS

Leibowitz et al., "Night Myopia and the Intermediate Dark Focus of Accomodation," Journal of the Optical Society of America, Oct. 1975, 65(10):1121-1128.

Wesner et al., "Instrument Myopia Conceptions, Misconceptions, and Influencing Factors," Documenta Ophthalmologica, Mar. 31, 1986;62(3):281-308.

International Search Report and Written Opinion of PCT Application No. PCT/US2008/061557, dated Nov. 26, 2008, 19 pages total.

* cited by examiner

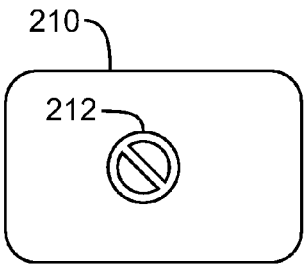 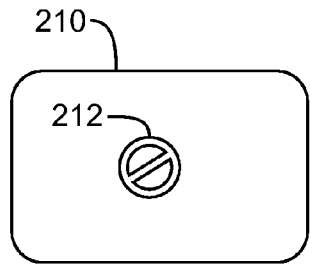 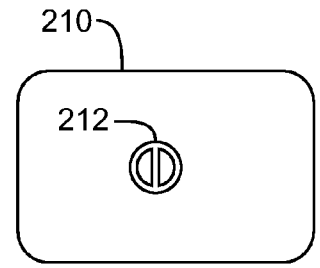
FIG. 5A   FIG. 5B   FIG. 5C
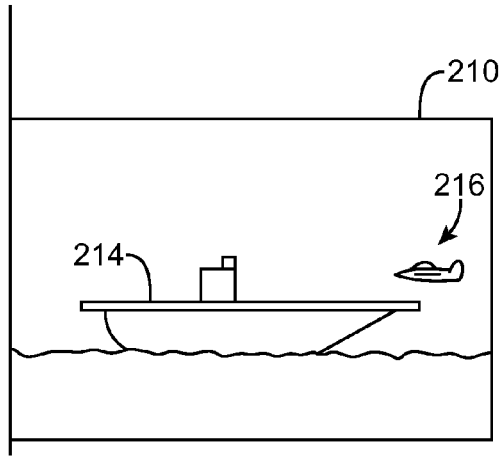 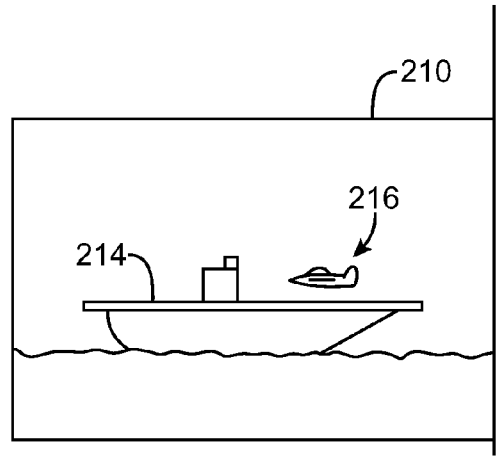
FIG. 5D   FIG. 5E
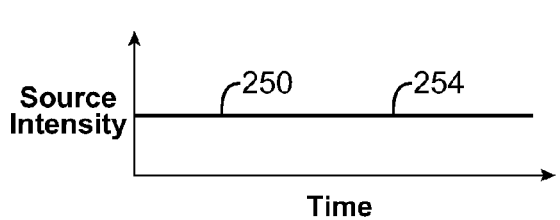 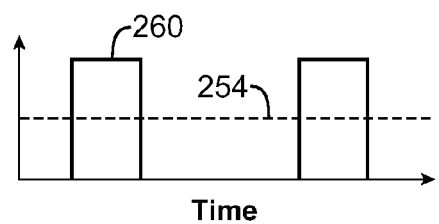
FIG. 6A   FIG. 6C
 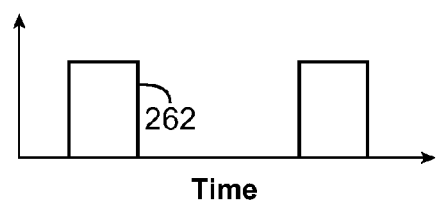
FIG. 6B   FIG. 6D

SYSTEM AND METHOD FOR ILLUMINATION AND FIXATION WITH OPHTHALMIC DIAGNOSTIC INSTRUMENTS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention relates to diagnosis and/or measurement of the optical properties of the eye. Embodiments of the present invention provide systems, devices, and methods to measure, diagnose and treat optical properties of an eye. Although specific mention is made to wavefront measurements of the eye, embodiments of the present invention can be used with many instruments that measure and/or treat optical properties of the eye, for example auto refractors and laser eye surgery systems.

The eye has many transparent tissue structures that are shaped to form images on the retina. Many of these tissue structures, such as the cornea and crystalline lens each contribute to the optical properties of the eye. Accurate measurements of these tissue structures and the overall refractive properties of the eye can be very helpful in the diagnosis and/or correction of optical defects of the eye. In some instances, the optical characteristics of the eye may change and can make accurate measurements of the eye difficult. For example, as patients age cataracts may form in the crystalline lens of the eye, and the cataracts may scatter light from a measurement device so as to degrade measurements of the eye.

The human eye is trained maintain focus on an object that it sees, even when the distance from the object to the eye changes. To maintain focus on an object, the crystalline lens of the eye may move and/or change shape so as to maintain focus. This ability of the eye to adjust and focus on a visual stimulus can be referred to as accommodation. Although the exact mechanism of accommodation has been debated in the scientific literature, one widely held view is that the eye may be considered in a relaxed state while viewing a distant object and muscles of the eye can contract to accommodate in response to a near object.

The accommodative state of the eye can effect the measured refractive properties of the eye. As accommodation changes the focus of the eye, a patient who has good distance vision with no refractive error can become myopic, or nearsighted, when the eye of the patient accommodates and focuses on a near object. In some instances, for example with instrument myopia, the patient may look into an instrument that is close to the patient and the eye may accommodate and adjust to near focus so as to become myopic while looking into the instrument, even though the fixation target of the instrument is positioned far from the patient.

With measurements of refractive properties of the eye, it can be desirable to make these measurements while accommodation the eye is relaxed and adjusted for distance vision. With correction of refractive error of the eye, it is often desirable to correct the patient's vision such that the patient will have good distance vision while accommodation of the eye is relaxed. This correction allows the patient to have good distance vision and use his or her accommodation to focus on near objects.

If a patient's eye accommodates for near vision during measurements of the eye's refraction, the patient may receive an improper amount of optical correction that can make the treatment less than ideal. For example with nearsightedness, overcorrection of the patient can result from patient accommodation for a near target during the refractive measurement of the eye. This overcorrection can make the patient far sighted, or hyperopic, once the accommodation relaxes. Consequently, the patient may not have good near vision as the patient may be unable to overcome the overcorrection to see objects that are near.

With the diagnosis and treatment of hyperopia, hyperopic patients often accommodate during both near and far vision so as to compensate for their hyperopia, such that these patients may have trouble relaxing their accommodation during measurements, even when viewing targets at a distance. Consequently, residual amounts of hyperopia may not be detected. Incomplete assessment of hyperopia can result in under correction and incomplete treatment of the patient's hyperopia, and the patient may need subsequent treatment as the patient ages and loses the ability to accommodate.

Many techniques can be used to decrease accommodation of the eye. For example, cycloplegic drops can be placed in the eye to paralyze an accommodative response of the eye. While effective, cycloplegic drops may often have side effects that can be undesirable for the patient. For example, the patient may not be able to read with distance correction, and pupil dilation resulting from such drops can make some patients sensitive to bright lights.

Another approach to minimize and relax accommodation during measurement of the eye is to provide a target at a distances that are progressively farther from the patient. This technique can be referred to as fogging the patient, in that the perceived target becomes blurry to the patient and the patient will tend to relax any accommodation to bring the more distant fogged target into focus. While fogging can be effective for many patients, some patients may not respond well to this technique.

Some measurement systems use light beams that may be at least partially visible to the patient and potentially interfere with the measurements of the eye. In some patients and measurement systems, visible measurement beams that are perceived by the patient may provide a visual stimulus in addition to the fixation target and interfere with the measurement of the patient. Although infrared light beams may be used that are invisible to the patient, the eye may refract and scatter infrared light differently than visible light, such that measurement errors can occur.

In light of the above, it would be desirable to have improved methods, devices, and systems for diagnosis and/or treatment of refractive error, aberrations, and other vision defects of the eye. It would also be desirable to have improved methods, devices, and systems for measuring the optical and/or visual response of the human viewing system and for developing new prescriptions to treat refractive error, aberrations, and other viewing defects. It would generally be desirable to increase the percentage of the population which can be effectively treated for refractive error, aberrations and other vision defects without greatly increasing the cost, risk, and/or complexity of diagnosis and/or treatment over current techniques. It would also be beneficial to have improved measurement devices and systems which enhanced the speed, ease of use, accuracy, and efficiency of obtaining wavefront measurements of a patient's eye, ideally while lowering the overall costs of such measurements.

BRIEF SUMMARY OF THE INVENTION

The present invention generally provides improved devices, systems, and methods for measuring, diagnosing, and/or treating refractive error, aberrations and other vision defects. The devices, systems and methods of embodiments of the present invention are particularly well-suited for measuring refractive optical aberrations of the eye and can be well-suited for developing general or customized prescriptions for treatment of vision defects. In some embodiments, the devices, systems and methods of the present invention will make use of a target on a display that moves transverse to an optical path from the display to the eye, so as to relax accommodation of the lens of the eye. The patient may be fogged while the target moves transverse to the optical path on the display, and the target may become smaller such that the patient perceives the target to be moving away from the patient. Many kinds of transverse target motion can be employed including translation and rotation of the target shown on the display. In some embodiments, a pupil camera measures eye position that can be correlated with the position of the target on the display to determine that the patient has maintained fixation on the moving target. In some embodiments, a measurement light beam may be pulsed subsequent to and/or during motion of the target that relaxes accommodation of the eye so as to avoid interference of the measurement light beam with the target on the display. In some embodiments, a common timing signal is used to synchronize the pulsed measurement beam with measurement cameras and movement of the target. The pulsed measurement light beam may have a short duration and use an intensity that is higher than a safety threshold for a long pulse of the light beam. Work in relation with embodiments of the present invention indicates that such short measurement beam pulses may freeze at least some of the motion of the eye and can provide substantial detail for accurate measurement of the aberrations of the eye. In addition the use of short measurement pulses can provide a signal with less noise in the presence of a cataract or other light scatting medium that can degrade the quality of spots and or images from the eye.

In a first aspect, embodiments of the present invention provide an optical device to diagnose an eye of a patient. The device comprises a display with a target visible to a patient. An optical system projects the target along an optical path from the display to the patient. The display moves the target transverse to the optical path. A sensor measures optical aberrations of the eye in response to movement of the target transverse to the optical path.

In some embodiments, transverse movement of the target comprises at least one of a translation or a rotation. The display may comprise a microdisplay with pixel elements. The display may comprise a computer addressable display with pixel elements that move the target across the display. The display may comprise at least one of an organic light emitting diode microdisplay, a liquid crystal microdisplay, a liquid crystal on silicon microdisplay, or a MEMS micro display.

In some embodiments, a processor is configured to move the target transverse to the optical axis and measure the optical properties of the eye. The processor can be configured to rotate virtually a target object on the display. The processor can be configured to decrease a size of the image while the optical system fogs the target. The processor can be configured to correlate a position of the target transverse to the optical path with a position of the eye. The processor may be configured to adjust a vergence of the target with the optical system and measure a range of accommodation of the eye in response to the vergence of the target.

In specific embodiments, the display comprises a stationary scene while the target moves transverse to the optical axis. A sensor may measure a position of the eye as the target moves transverse to the optical axis.

In another aspect, embodiments of the present invention provide a method of diagnosing an eye with a sensor. A target is presented on a display to a patient. The target is projected along a path from the display to the patient. The target is moved transverse to the optical path to relax an accommodation of the eye. Optical aberrations the eye are measured with the sensor.

In some embodiments, the target is moved transverse to the optical path with at least one of a translation or a rotation. The display may comprise a stationary scene while the target moves transverse to the optical path.

In another aspect, embodiments of the present invention provide an optical device to diagnose an eye of a patient. The device comprises a display with a target visible to a patient. An optical system projects the target display along an optical path from the display to the patient. A sensor measures optical aberrations of the eye. A pulsed measurement light source is coupled to the measurement sensor and visible to the patient. The pulsed light source is pulsed while the target is configured to relax an accommodation of the eye of the patient.

In some embodiments, the pulsed measurement light source is synchronized with the target. The optical system can be adapted to fog the target to relax the accommodation of the eye. The pulsed light source can be synchronized with the sensor, and the pulsed light source can be synchronized with a frame transfer rate to a processor. The light source may comprise at least one of a laser, a super luminescent diode or a light emitting diode. The sensor may comprise at least one of a Shack-Hartmann wavefront sensor, a Tscherning aberrometer, or a spatially resolved refractometer.

In yet another aspect, embodiments of the present invention provide a method of diagnosing an eye of a patient with a sensor. The method may comprise presenting a target on a display with the target visible to the patient. A light source that is visible to the patient is pulsed to measure aberrations of the eye while the target is configured to relax an accommodation of the eye of the patient.

In some embodiments, the target moves transverse to an optical path from the target to the patient. The light source can be pulsed in response to a common timing signal, and the target may move transverse to the optical path in response to the common timing signal.

In a further aspect, embodiments of the present invention provide an optical device to diagnose aberrations of an eye of a patient. The device comprises an aberration sensor to measure the optical aberrations of the eye. A pulsed measurement light source is synchronized with the measurement sensor. The pulsed light source may be pulsed for a short duration to avoid visual interference with a fixation target.

In specific embodiments, the pulsed measurement light source can be adapted to pulse a few times with each pulse synchronized to a separate frame of the sensor. A duration of each pulse of the measurement light source may correspond to no more than about 30% of a duration of the separate frame of the sensor. The short pulse may comprise a short duration no more than about 100 ms and the long pulse threshold may correspond to a long duration of at least about 500 ms. The pulsed measurement light source may comprise infrared light.

BRIEF DESCRIPTION OF THE DRAWINGS

FIGS. 5A to 5C show a target with rotational motion and decreasing size on the display, according to embodiments of the present invention;

FIGS. 5D and 5E show a target with translational motion on the display, according to embodiments of the present invention;

FIGS. 6A and 6B show a long pulse measurement beam and camera timing signal, according to embodiments of the present invention;

FIGS. 6C and 6D show a short pulsed measurement light beam and camera timing signal, according to embodiments of the present invention;

DETAILED DESCRIPTION OF THE INVENTION

The present invention generally provides devices, systems, and methods for diagnosing, measuring and/or treating one or both eyes of a patient. The invention allows measurement of the eye with the measurement system positioned near the eye while the eye is relaxed so as to relax an accommodative response of the eye. The invention also allows accommodation of an eye to be objectively determined, optionally based on measurements of the ocular optics. Embodiments of the present invention also allow candidate refractive eye prescriptions to be evaluated objectively and/or subjectively, often without having to fabricate one or more individual test lenses, even when customized prescriptive shapes are to be implemented and evaluated at a plurality of viewing conditions (such as different viewing distances, lighting conditions, and the like). Hence these embodiments of the present invention will find applications for measuring and treating a variety of defects of the eye, including presbyopia, spherical errors (including myopia and hyperopia), regular and irregular astigmatism, high-order aberrations, and the like, and may also find advantageous use for retinal or neural processing disorders such as age-related macular degeneration (AMD), and the like.

Many embodiments of the present invention will make use of adaptive optics systems such as those including a deformable mirror or the like. Adaptive optics systems are well-suited for measuring a patient's ocular aberrations, often by driving the deformable mirror to a configuration which compensates for the overall aberration of the eye. Using an adaptive optics system, the patient may view optometric test targets, such as an eye chart, to test the subjective visual acuity and contrast sensitivity. Optical surfaces for presbyopia correction may be provided by theoretical derivation, optical modeling, empirical clinical trials, or the like, and these presbyopia-mitigating shapes may be verified with the techniques of the present invention to ensure that the patient obtains satisfactory near, intermediate, and distance vision.

Embodiments of the present invention can be readily adapted for use with existing laser systems, wavefront measurement systems, and other optical measurement and therapeutic devices. While the systems, devices, software, and methods of embodiments of the present invention are described primarily in the context of a diagnostic measurement system, it should be understood that embodiments of the present invention may be adapted for use in eye treatment procedures and systems, such as laser vision correction, spectacle lenses, intraocular lenses, contact lenses, corneal inlays and onlays, corneal ring implants, collagenous corneal tissue thermal remodeling, and the like.

Figure 1:
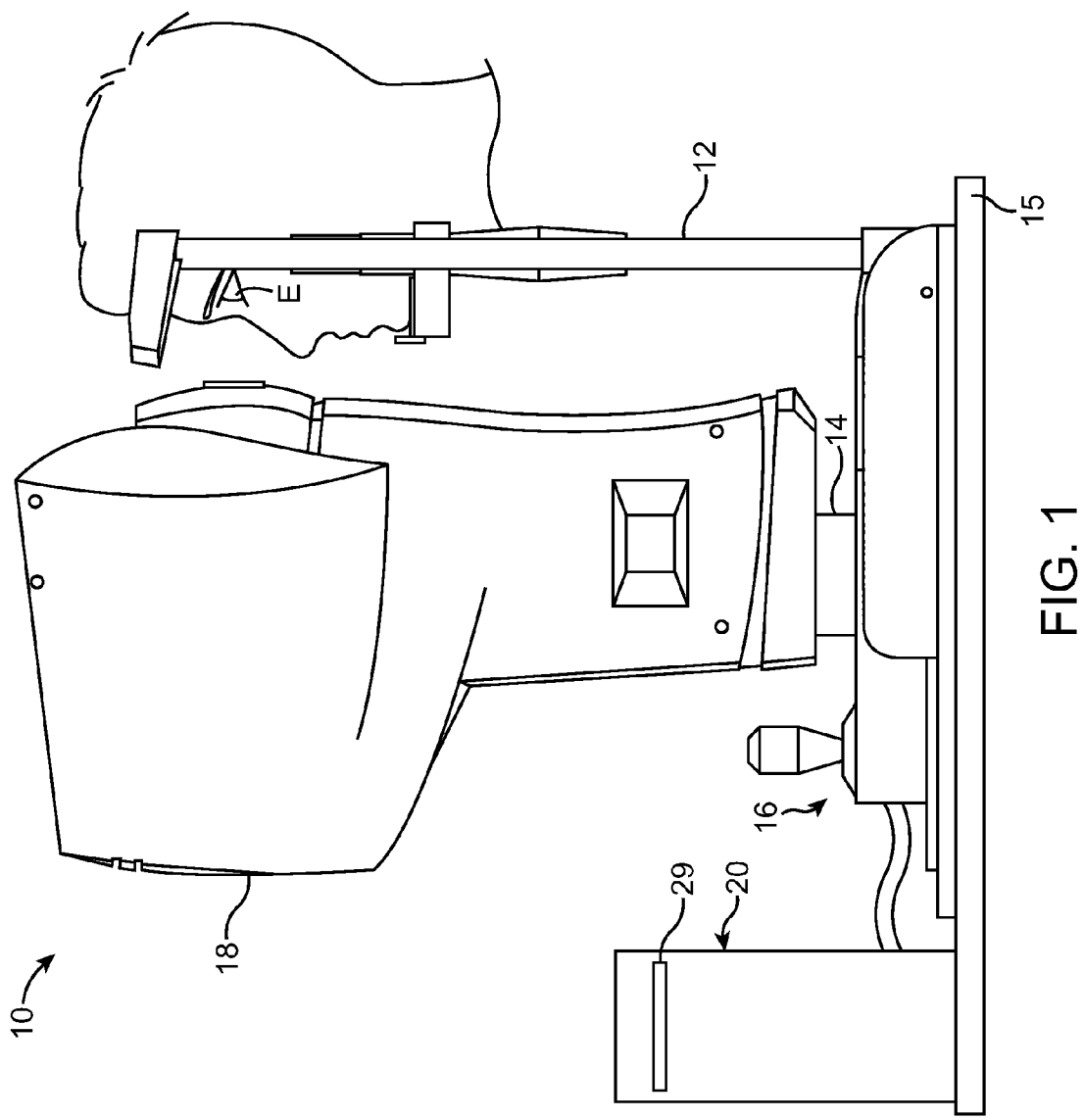
FIG. 1 illustrates a wavefront measurement system, according to embodiments of the present invention.

Referring now to FIG. 1, a wavefront measurement system 10 is shown, according to embodiments of the present invention. Wavefront measurement system 10 includes a patient support 12 to support the head and thereby an eye E of the patient. One will appreciate that components of system 10 are placed in proximity to the patient, such that the patient may perceive that components of system 10 are nearby, and in some instances the patient may be inclined to accommodate in response. Patient support 12 may comprise many known methods of supporting a patient including chin rests, beds, bite bars and the like. In some embodiments, a diagnostic instrument head 18 may comprises optical components and sensors to measure the eye. In some embodiments, diagnostic instrument head 18 comprises an image sensor, for example a charge coupled device (CCD) array that can be used to align the eye. A support 14 may support diagnostic instrument head 18. A table 15 supports patient support 12 and a linkage 16. Linkage 16, support 14 and instrument head 18 are connected to patient support 12 with table 15. Linkage 16 can move with independent translation in three dimensions, X, Y and Z, so as to move instrument head 18 in relation to eye E. Alternatively or in combination, the patient support may be moved.

A computer system 20 can be connected to instrument head 18 Computer system 20 may comprise a tangible medium 29 for storing instructions, data and the like. Computer system 20 can be connected to instrument head 18 with a cable or via various wireless technologies.

Figure 2:
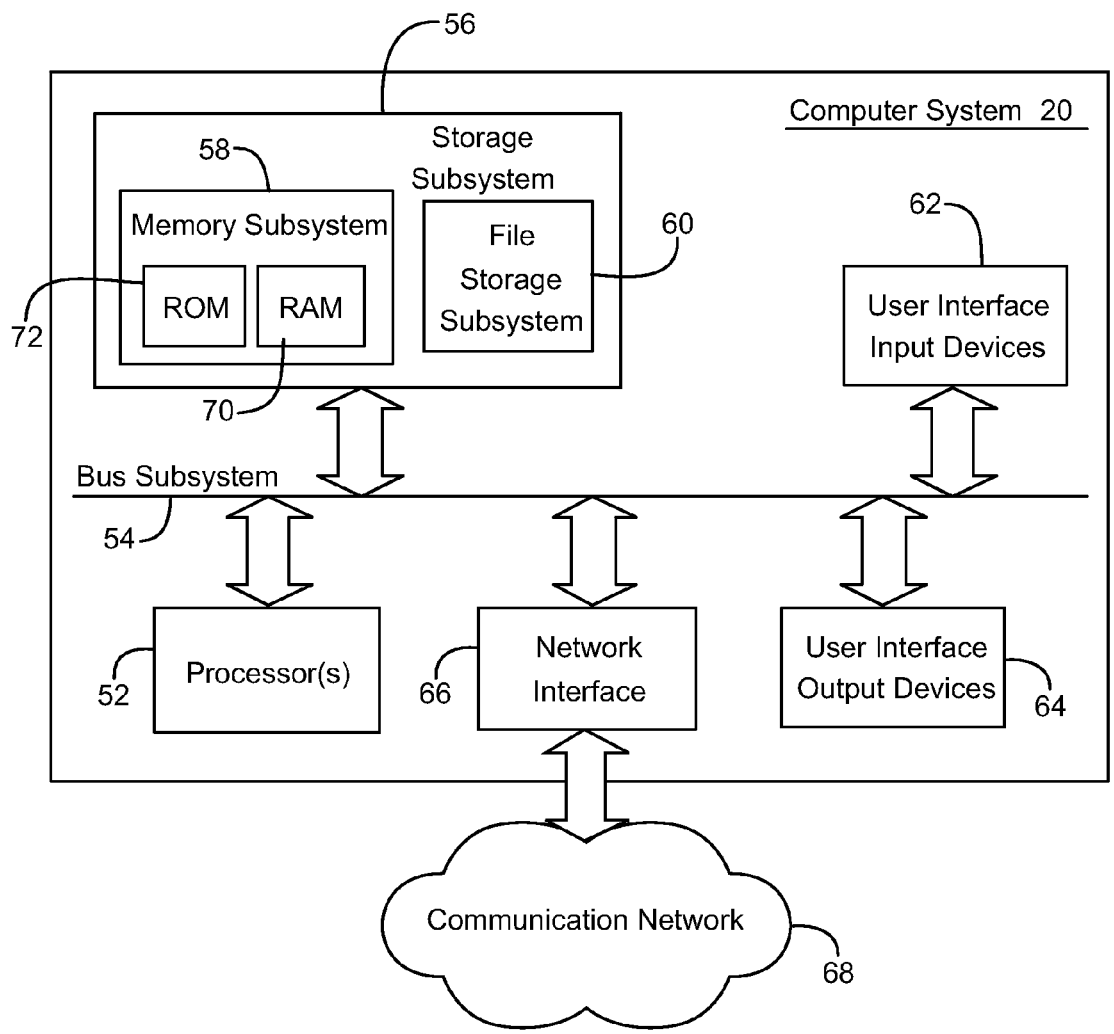
FIG. 2 illustrates a computer system as in FIG. 1, according to embodiments of the present invention.

FIG. 2 is a simplified block diagram of computer system 20 that may be used by the wavefront measurement system 10, according to embodiments of the present invention. Computer system 20 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 10.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 20.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 20 to a user.

Storage subsystem 56 stores the basic programming and data constructs that provide the functionality of the various embodiments of the present invention. For example, a database and modules implementing the functionality of the methods and embodiments of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 20. The modules implementing the functionality of the present invention may be stored by file storage subsystem 60.

Bus subsystem 54 provides a mechanism for letting the various components and subsystems of computer system 20 communicate with each other as intended. The various subsystems and components of computer system 20 need not be at the same physical location but may be distributed at various locations within a distributed network. Although bus subsystem 54 is shown schematically as a single bus, alternate embodiments of the bus subsystem may utilize multiple busses.

Computer system 20 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 20 depicted in FIG. 2 is intended only as a specific example for purposes of illustrating one embodiment of the present invention. Many other configurations of computer system 20 are possible having more or less components than the computer system depicted in FIG. 2.

Figure 3:
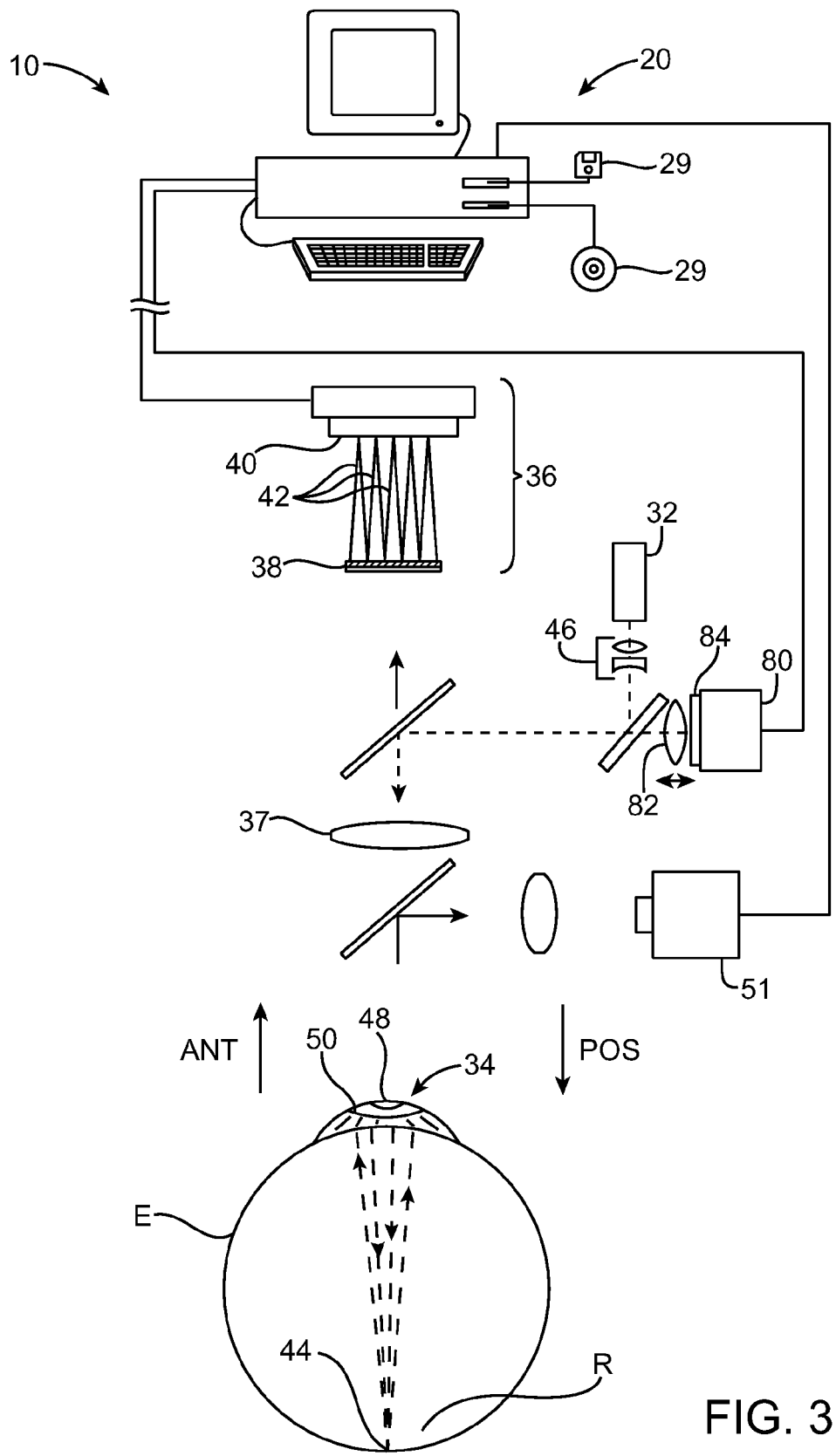
FIG. 3 illustrates components of a wavefront measurement system as in FIG. 1, according to embodiments of the present invention.

Referring now to FIG. 3, components of wavefront measurement system 10 are schematically illustrated in simplified form. In very general terms, wavefront measurement system 10 is configured to sense local slopes of a gradient map of an optical wavefront exiting the patient's eye. Measurement system 10 presents a visual target 84 on a display 80 to the eye such that eye can relax accommodation of the lens. Although measurement system 10 may be positioned near the eye, the visual target may be adjusted to appear distant to the patient, such that the accommodative reflex of eye is relaxed. In the relaxed state, aberrations of the eye can be accurately measured.

Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map. In some embodiments, the wavefront system may comprise an array of apertures without lenslets to sample the local slopes of the gradient map. Wavefront measurement system 10 includes an image source 32, such as a laser, to project a point source onto the retina, and display 80 with target 84 that presents a visual stimulus to the patient, such as a moving target, to relax accommodation of the eye.

Display 80 can be coupled to the processor, and pixels of display 80 can be illuminated to define the target under control of the processor. Display 80 may comprise at least one of an organic light emitting diode (OLED) microdisplay, a liquid crystal (LCD) microdisplay, a liquid crystal on silicon (LCOS) microdisplay, a cathode ray tube (CRT), a projection system, or a micro-electromechanical system (MEMS) microdisplay. Lens 82 can move along the optical path to adjust fogging of the target by introducing additional positive optical power in front of the eye. In some embodiments, as lens 82 moves toward the target on the display, the image of the target seen by the patient moves along the optical path such that the target appears farther from the patient. As light projected from image light source 32 may not be affected by lens 82, the image light source may not be fogged along with the target shown on the display. In some embodiments, image light source 32 is pulsed after the target has translated across display 80 and after lens 82 has moved to fog the target, so as to relax an accommodation of the eye. This pulsing of the source after display 80 and lens 82 have relaxed the eye can avoid an accommodation of the eye in response to the fixation target.

Image source 32 can project a point source image through optical tissues 34 of eye E so as to form a point source image 44 upon a surface of retina R. Image source 32 may comprise many light sources including a laser, a super luminescent diode, a light emitting diode and the like. In some embodiments, image source 32 generates near infrared light that can be perceived by the patient, although visible to mid infrared light can be used.

The image from retina R is transmitted by the optical system of the eye (e.g., optical tissues 34) and imaged onto a wavefront sensor 36 by system optics 37. In some embodiments, system optics 37 may comprise components of a Badal Optometer that can correct for second order spherical aberration of the eye and maintain substantially constant magnification of images projected to and from the eye over a range of spherical aberration from about −15 to +5 Diopters.

The wavefront sensor 36 communicates signals to computer system 20 for measurement of the optical errors in the optical tissues 34 and/or determination of an optical tissue ablation treatment program. Computer system 20 may be in communication with an additional computer system and/or processor, for example a processor that directs the laser surgery. Some or all of the components of computer system 20 or the wavefront measurement system 30 may be combined or separate, for example computer system 20 may comprise physically separated components in electronic communication over the Internet. Tangible medium 29 may comprise a floppy disk drive, CD-ROM or the like. If desired, data from wavefront sensor 36 may be transmitted to a laser computer system via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34, an image of the eye pupil P is similarly imaged onto a surface of lenslet array 38, the lenslet array separates the transmitted image into an array of beamlets 42, and (in combination with other optical components of the system) images the separated beamlets on the surface of sensor 40. In some embodiments, sensor 40 comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue. Alternatively or in combination, spot size, intensity, shape and/or other spot characteristics may be used to determine additional information on the wavefront and/or local gradients.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

The wavefront data may be stored in a computer readable medium 29 or a memory of the wavefront sensor system 30. The data may be stored in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. In some embodiments, such information contains all the available information on the wavefront error of the eye and is sufficient to reconstruct the wavefront or any portion of it. In such embodiments, there may not be a need to reprocess the Hartmann-Shack image more than once, and the data space used to store the gradient array is not large. For example, to accommodate an image of a pupil with an 8 mm diameter, an array of a 20×20 size (i.e., 400 elements) can be sufficient. As can be appreciated, in some embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target so as to change a distance from the eye to the target as described in that reference, optical characteristics of the eye may be determined while the eye accommodates or adapts to image a field of view at a varying distance and/or angles.

The location of the optical axis of the eye may be verified by reference to the data provided from a pupil camera 51. In the exemplary embodiment, a pupil camera 51 images pupil 50 so as to determine a position of the pupil for registration of the wavefront sensor data relative to the optical tissues. In some embodiments, pupil camera 51 can be used to determine and/or correlate the position of the eye in response to a position of the target to determine whether the eye is looking at the moving fixation target.

Figure 3A:
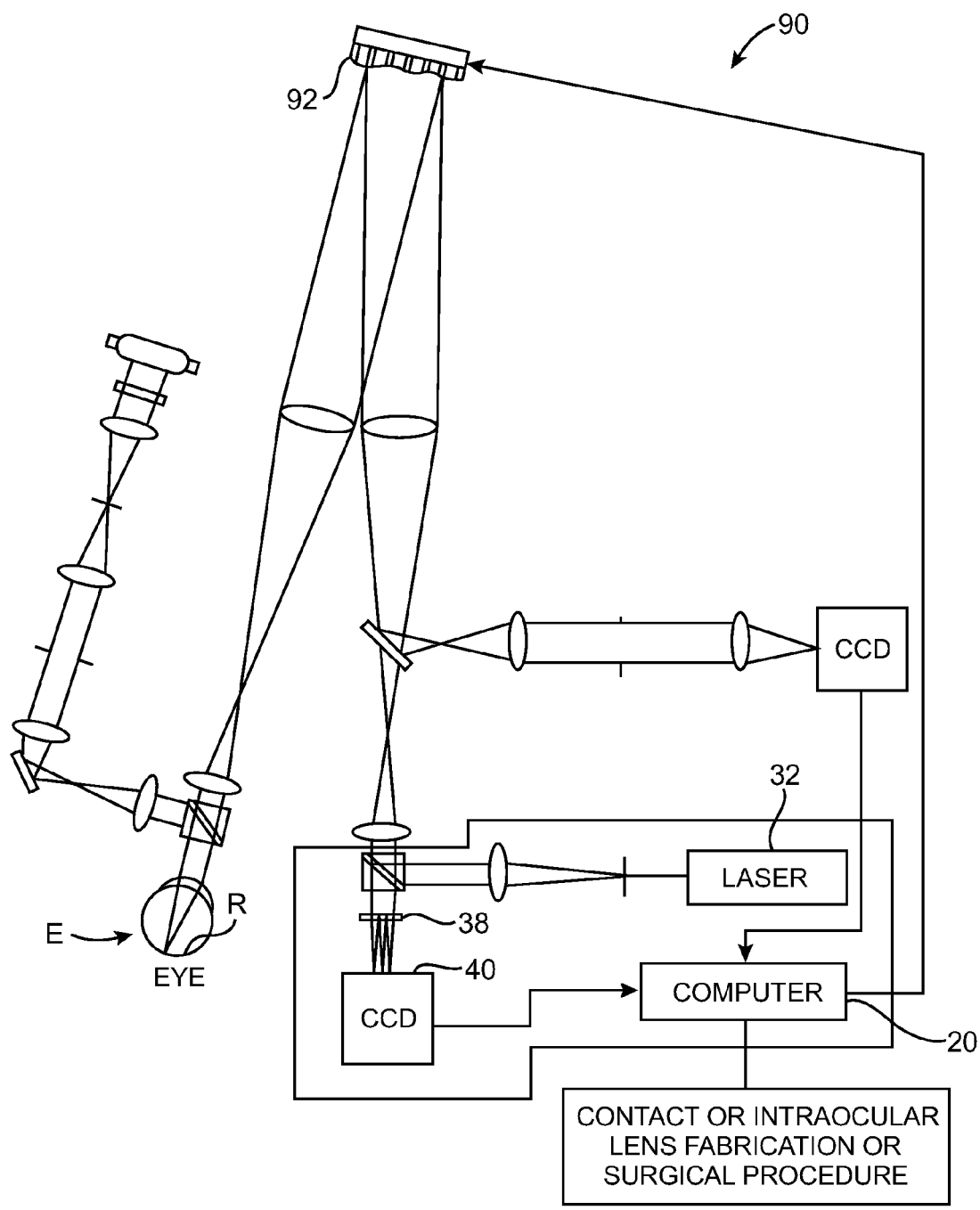
FIG. 3A illustrates wavefront measurement system with a deformable mirror, according to embodiments of the present invention.

An alternative embodiment of a wavefront measurement system is illustrated in FIG. 3A. The major components of the system of FIG. 3A are similar to those of FIG. 3. Additionally, FIG. 3A includes an adaptive optics system 90 which comprises a deformable mirror. The source image is reflected from deformable mirror 92 during transmission to retina R, and the deformable mirror is also along the optical path used to form the transmitted image between retina R and imaging sensor 40. Deformable mirror 92 can be controllably deformed by computer system 20 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference. Alternatively, or in combination, separate adaptive optical elements and/or separate optical paths may be used for the light beams toward and away from the eye.

The components of an embodiment of a wavefront measurement system for measuring the eye and ablations comprise elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Wavefront measurement systems suitable for incorporation of embodiments of the present invention include the Zyoptix® Systems commercially available from Bausch & Lomb of Rochester N.Y.; the OPD Scan II™ commercially available from NIDEK of Gamagori, Japan; the WASCA™ analyzer, commercially available from Carl Zeiss Meditec, Inc. of Dublin, Calif.; the iTrace™, commercially available from Tracey Technologies, Inc. of Houston, Tex.; the ORK™ system from Schwind; and the Wavelight Allegretto™ system and related aberrometer.

Figure 4:
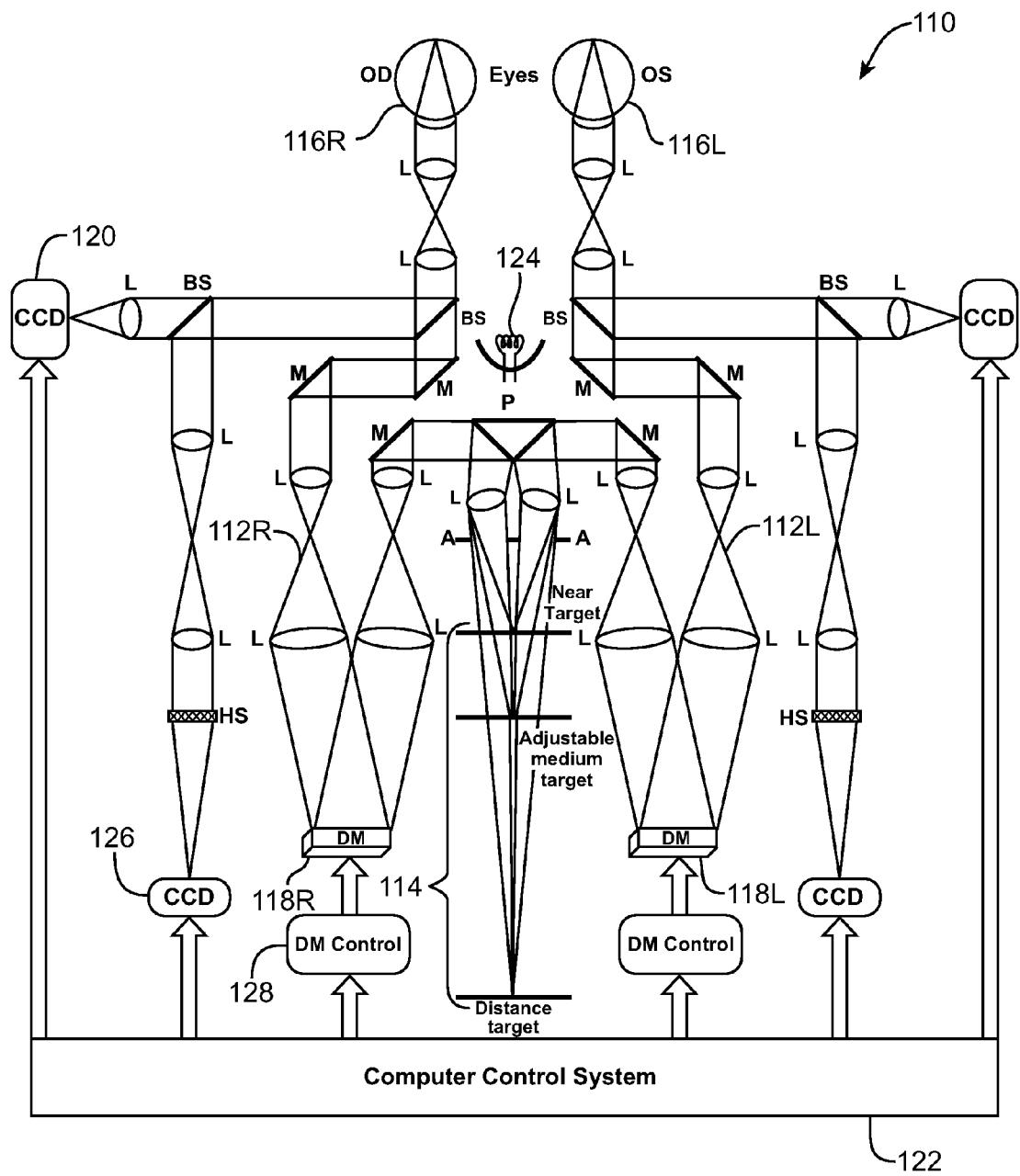
FIG. 4 schematically illustrates a binocular ocular measurement and diagnostic apparatus for measuring accommodation and aberrations of the eye, according to embodiments of the present invention.

FIG. 4 schematically illustrates a binocular ocular measurement and diagnostic apparatus for measuring accommodation and aberrations of the eye, according to embodiments of the present invention. An adaptive optics apparatus 110 generally includes an optical path 112R coupling an adjustable target 114 with a right eye 116R of a patient. A similar optical path 112L couples adjustable target 114 with a left eye 116L, thereby providing a binocular viewing system. As the components of the optical path, sensors, and the like of apparatus 110 along the right optical path 112R are generally similar to those of the left optical path 112L, only the right side need be described to understand the structure and use of the apparatus. In some embodiments, the components of FIG. 4 may be used in a monocular system.

Optical path 112R includes a series of lenses L and mirrors M optically coupling adjustable target 114 to right eye 116R via a deformable mirror 118R. A Hartmann-Shack wavefront sensor HS is coupled to optical path 112R by a beam splitter BS for measurement of aberrations of eye 116R. A sensor 120 is also coupled to the optical path 112R by one or more beam splitters BS for measurement of a size of a pupil of eye 116R, and may also be used to determine a position of the eye and the like, as described above regarding the wavefront measurement system of FIG. 3.

Adjustable target 114 transmits an image along optical path 112R, with the light being profiled by an aperture A having a field stop, the light then being collimated by an adjustable focal-length lens L before being directed along the optical path using a prism P. At the end of the optical path adjacent eye 116R, the light is re-collimated by lenses L to go through the optics of the eye, primarily the cornea and the lens of the eye, so as to form an image on the retina.

When apparatus 110 is used for subjective measurements, light from the retina goes back through the ocular optics and adjacent lenses L of optical path 112R, and is split from the optical path by a first beam splitter BS. This retinal image light is split into two channels by a second beam splitter BS. A first of these two channels is directed by a lens L to sensor 120 for imaging the pupil, the sensor often comprising a charged couple device (CCD), a pupilometer, and/or the like. The second channel is directed from beam splitter BS via adjacent lenses L to Hartmann-Shack wavefront sensor HS.

When the deformable mirror is in a flat configuration, an initial total ocular aberration measurement can be taken of eye 116R, often using adjustable target 114 in a distant viewing configuration. Using this initial measurement, the deformable mirror can be configured to compensate for ocular aberrations. When adjustable target 114 is moved to an intermediate distance, any residual accommodation may kick in. With a near light source, the full residual accommodation of the eye may be employed when the patient tries to focus on the target, particularly if the target is at or beyond the near viewing accommodation of the eye. If the Hartmann-Shack wavefront sensor HS measures the aberration of the eye while the lens of the eye is in its nearest viewing configuration, the total change in the ocular aberration between the distance viewing measurement and the near viewing measurements allows an objective determination of a residual accommodation. Note that the eye can, but need not necessarily be fogged by gradually increasing the viewing distance to just beyond the accommodation range. Instead, predetermined viewing distances (such as a distance viewing configuration of greater than 8', optionally at about 20'; and a near viewing configuration of less than 5', often being less than 2', and optionally being about 16") may be sufficient for measuring the change in ocular aberration for the eyes of some or all patients, particularly patients at or above a predetermined age (such as over an age of 30, often being over an age of 45).

Adjustable viewing target 114 will often include a light source of visible light such as a light emitting diode (LED), a laser diode, and incandescent or fluorescent bulb, or the like. Optionally, the light source of adjustable target 114 is adjustable in brightness level and/or viewing distance. Adjustable target 114 will typically have an input for varying of the viewing distance and/or brightness level, with the input often being coupled to a computer control system 122. In other embodiments, adjustment of the brightness level or viewing distance may be effected by a manual input, a turret of alternatively selectable lenses, filters, holographic optical elements, or the like. If adjustable target 114 is not under the control of computer control system 122 (by coupling of an input of the adjustable target to a control signal output of the computer system), then the adjustable target will often transmit a signal to a computer so as to indicate the viewing configuration of the target during measurements. In some embodiments, adjustment of the brightness level may be effected using one or more ambient lights 124, with the input for adjusting brightness level optionally being coupled to ambient light 124 and an adjustable brightness light source of target 114, or by using a fixed brightness light source within target 114 in combination with ambient light 124 so as to alter an overall brightness level to eyes 116R, 116L.

Adjustment of the ambient and/or target viewing brightness level allows apparatus 110 to measure pupil size and/or aberrations under different brightness level viewing conditions. As the brightness level of the viewing target or ambient light increases, pupil size decreases. Additionally, as eyes adjust from a near viewing distance to a far viewing distance, pupil size may decrease. Apparatus 110 may be used in a room having a low or darkened room lighting to facilitate low brightness level measurements, or a housing or drape may be provided to limit the effect of room lighting on the eye. In some embodiments, ambient light may be used to adjust and/or control pupil size.

Measurement of eyes at a matrix of different viewing conditions will facilitate, customized prescriptions for the patient's eyes. Preferably, pupil measurements and/or aberration measurements will be made at a plurality of viewing conditions, preferably at least 2, preferably at least 3 or more different viewing conditions, ideally at 4 or more viewing conditions. This may facilitate development or selection of presbyopia and other refractive defect mitigating shapes for the eye which are well-suited for typical tasks at multiple viewing conditions. For example, the prescriptive shape may be selected so as to provide good acuity for reading, (often without reading glasses) at a relatively bright, near viewing configuration of the pupil and ocular optics; ideally while also providing good visual acuity for reading signs at a far distance and/or dashboard instruments at an intermediate distance when driving at night; while also maintaining the best available distance viewing acuity under bright-light conditions. Hence, more than one accommodation of each eye 116R, 116L may be measured so as to indicate the adjustability of the lens and other ocular optics of the eye at different lighting conditions.

Adjustable target 114 will often be configured so as to provide three types of viewing distances: near viewing (typically at less than about 2 feet, often at about 16 inches), distant viewing (typically at greater than about 5 feet, often at about 8 feet or more, optionally at 10 feet or more, and in some embodiments at about 20 feet or more), and an intermediate or medium viewing distance. The intermediate viewing distance may be adjustable to a plurality of different settings or throughout a range. The intermediate viewing distance of adjustable target 114 will often be adjustable within a range of about 2 to about 8 feet, often being adjustable within a range from about 32 inches to about 5 feet. Actual linear distance along optical path 112R between eye 116R and adjustable target 114 need not necessarily correspond with the optical viewing distance, as lenses L, mirrors M, or other optical elements may be used to adjust the optical viewing distance. Hence, the light source and field stop of adjustable target 114 may remain the same actual linear distance apart throughout the near, intermediate, and distance viewing configurations using a zoom lens arrangement, selectable turret, or the like.

Adjustable target 114 may have a plurality of target images, including images that rotate, translate and change size. A display can be coupled with a measurement light beam using a beam splitter, as described above. The display can provide targets that move transverse to the optical path and/or the optical axis that extends from the display to the patient, for example as described with reference to FIGS. 5A to 5E. To facilitate wavefront measurements, adjustable target 114 may include a spot target image projecting a spot of light on the retina of eyes 116R, 116L. The spotlight image may then be used by Hartmann-Shack sensor HS together with its associated image capture device such as a CCD 126 and a related analysis module of computer 122 for measuring wavefront aberrations, as described above. Hence, this image may comprise an aberration measurement image. Along with an aberration measurement image, adjustable target 114 may also include any of a wide variety of verification test image shapes such as one or more letters of a Snellen eye chart, a landscape image (particularly for distance viewing), a portrait image (such as for intermediate viewing) small text or detail image (for example, for verifying near visual acuity) and the like.

As visual performance may depend on alignment of eye 116R with deformable mirror 118R and the verification image, the visual evaluation images may be modified. In some embodiments, rather than having the eye scan the various lines of letters in the Snellen eye chart at adjustable target 114 (and thereby moving into and out of alignment with the deformable mirror 118R), the eye chart may move or only one letter of the eye chart may be shown at a time. This may help the deformable mirror to accurately compensate for high-order aberration of the eye, as well as maintaining an aspherical or multifocal candidate presbyopia-mitigating shape modeled by deformable mirror 118R at desired axial alignment with the eye, and/or the like. In some embodiments, visually acuity may be measured without the deformable mirror.

A number of different deformable mirrors or active mirrors may be used, including first or second generation membrane or foil mirrors, microchip mirrors having 100,000 or more facets, and the like. In the exemplary embodiment, deformable mirror 118R may comprise a system such as that available commercially from XINETICS, INC. located at Devens, Mass. Alternative deformable mirrors may be available commercially from BOSTON MICROMACHINES, located at Watertown, Mass., or from the FRAUNHOFER-INSTITUTE FOR PHOTONIC MICROSYSTEMS, of Dresden, Germany. Rather than using a deformable mirror, other forms of adaptive optics may also be employed. In some embodiments, the eye may be measured without adaptive optics.

The CCD of sensor 120 may include or be coupled to image analysis software and/or hardware so as to allow sensor 120 to measure a size of the pupil of the eye. Commercially available pupilometers may also be employed, including those available from PROCYON INSTRUMENTS, LTD., located in the United Kingdom, under model numbers P2000SA and P3000. Processing hardware and/or software modules such as image analysis software of sensor 120 may generally be resident in a processor of the associated sensor or CCD, in computer control system 122, or an intermediate processor coupling a sensor or controller to the elements of system 110 in a wide variety of alternative centralized or distributed data processing architectures.

Deformable mirror controller 128 can change the surface of deformable mirror 118R quite arbitrarily, so that is possible to create a surface of the deformable mirror which corresponds to and/or models a variety of candidate presbyopia-mitigating refractive shapes. Additionally, a deformable mirror can compensate for ocular aberrations of the eye as described above regarding FIG. 3A. Advantageously, controller 128 can configure deformable mirror 118R to combine an ocular aberration compensator with the candidate presbyopia-mitigating shape. Systems and methods for the mitigation of presbyopia are described in U.S. Pat. No. 6,280,435; entitled "Method and Systems for Laser Treatment of Presbyopia Using Offset Imaging;" U.S. Pat. No. 6,932,808, entitled "Ablation Shape for the Correction of Presbyopia"; and U.S. patent application Ser. No. 10/738,358, entitled "Presbyopia Correction Using Patient Data;" Ser. No. 11/134,630, "Residual Accommodation Threshold for Correction of Presbyopia and Other Presbyopia Correction Using Patient Data;" Ser. No. 10/872,331, entitled "Correction of Presbyopia Using Adaptive Optics and Associated Methods;" Ser. No. 11/173,904, entitled "Presbyopia Correction Through Negative High-Order Spherical Aberration;" and Ser. No. 11/134,027, entitled "Training Enhanced Pseudo Accommodation Methods, Systems and Devices for Mitigation of Presbyopia," the full disclosures of which are incorporated by reference.

When such a shape is applied to deformable mirror 118R, the patient will undergo an effect which is similar to the proposed treatment of the eye such as customized laser eye surgery, an intraocular lens, a contact lens, or the like. By configuring adjustable target 114 to a variety of different target distances and brightness levels, visual acuity and contrast sensitivity can be measured to examine the effectiveness of the overall proposed refractive correction for treatment of presbyopia. This allows the wavefront measurements to be used as a feedback signal, such as for reconfiguring the deformable mirror (and the corresponding candidate prescription). Processor 122 may include, for example, an optimizer module for deriving subsequent deformable mirror configurations. Suitable optimizer modules may comprise software and/or hardware configured for optimizing a deformable mirror shape using a Downhill Simplex method, a direction set method, a simulated annealing method, and/or the like. In the binocular system of 110, similar adjustments can be made to deformable mirror 118L to compensate for aberrations of the eye 116L, and to model a presbyopia-mitigating shape. The presbyopia-mitigating shape of the left eye may be the same as or different than that of the right eye. For example, where the left eye has a greater residual accommodation than the right eye, the strength of a candidate presbyopia-mitigating shape may be reduced as compared to that other eye. Furthermore, the binocular system of FIG. 4 allows the patient to determine acceptability of monovision systems which rely on one eye primarily for distance and the other eye for near viewing, and hybrid systems which use one approach (such as a central add region) for one eye and a different approach (such as peripheral add region) for the other eye to mitigate presbyopia (for example, see U.S. patent application Ser. No. 10/849,573, filed on May 18, 2004, entitled *Binocular Optical Treatment For Presbyopia*, the full disclosure of which is incorporated herein by reference). In some embodiments, the system of FIG. 4 may be used to model IOL correction in one eye and laser correction in the other eye.

FIGS. 5A to 5C show a target with rotational motion and decreasing size on the display, according to embodiments of the present invention. A display 210 shows a target 212 to a patient. Target 212 rotates about an optical axis near the center of display 210, such that target 212 moves transverse to the optical axis with an axis of rotation parallel to the optical axis. In some embodiments, rotational movement of the target in the plane of the display about an axis of rotation perpendicular to the display generally comprises movement of the target transverse to the optical axis. Target 212 may decrease in size and present a more distant perspective view while rotating about the optical axis. The rotation of target 212 may be about any axis relative to the visual axis of the patient. In some embodiments, the rotation may comprise virtual rotation of 3D target objects, and a different a perspective of a 3D target object may be seen by the patient as the 3D target object appears to rotate in front of the patient. The target perspective may become more distant as the target rotates, and the virtual image of the target shown on the display may comprise a perspective view of the target in which the perspective of the target becomes more distant as the target rotates. The system optics may fog the target with additional positive power while the size of the target decreases and the fogged target moves away from the patient along the optical axis. The additional positive power can be changed to zero. A push-pull technique may also be implemented in which the additional power changes sign and then becomes zero. The computer may monitor the focus of the eye continuously during the vergence change of the target. In some embodiments, instrument myopia can be eliminated for many eyes. The measurement information obtained may also be used to set accommodation to a desired state with adjustment to the system optics. In some embodiments, the system may capture and/or correlate eye movement and target distance with system measurements to determine the range of accommodation of the eye.

FIGS. 5D and 5E show a target with translational motion on the display, according to embodiments of the present invention. Display 210 shows an aircraft carrier 214 with a plane 216 to the patient. The plane is shown landing on a flight deck of the aircraft carrier. In some embodiments the aircraft carrier may move while the airplane lands on the aircraft carrier. In some embodiments, the aircraft carrier may remain stationary while the airplane lands on the aircraft carrier, and the aircraft carrier and ocean may comprise a stationary scene while the airplane target moves across the stationary scene. In some embodiments, objects in the scene can be added, changed and or removed, for example the plane can crash into the flight deck and burst into flames to draw the attention and fixation of the user. The scene may be of an airplane going away from the viewing eye as the plane lands or as the plane takes off. Such scenes may help to relax accommodation towards far viewing. One will recognize that a variety of alternate scenes may be used.

In some embodiments, the scene may cover an entire field of view so as to eliminate visual clipping, or vignetting, at the periphery of the scene. Work in relation with the present invention suggests that visual clipping of the scene may affect relaxation of the accommodative response as it may give the patient the impression that he or she is looking into a tunnel or a narrow device. In some embodiments, a window may be provided with open field viewing of a distance scene, for example a textured wall in the exam room, that is some distance from the patient so as to draw the attention of the patient away from the measurement instrument and toward the distant wall. This open field view can be coupled with the moving target on the display with a beam splitter, and the moving target presented to the patient and fogged, as described above, while the patient observes the distant scene on the wall with open field viewing.

FIGS. 6A and 6B show a long pulse measurement beam 250 and a camera timing signal 252, according to some embodiments of the present invention. System and methods for measuring wavefront aberrations are described in U.S. Pat. No. 6,052,180, entitled "Apparatus and Method for Characterizing Pulsed Light Beams;" and U.S. Pat. No. 6,598,975, entitled "Apparatus and Method for Measuring Vision Defects of a Human Eye;" and U.S. application Ser. No. 11/032,406, entitled "Method for Determining and Correcting Vision," the full disclosures of which are incorporated herein by reference. Long pulse measurement beam 250 may comprise an intensity that corresponds to a safety threshold 254 for a long pulse, for example a 500 ms or longer pulse. Camera timing signal 252 shows opening and closing of a camera shutter during the long pulse measurement beam. In such embodiments, the display can move the targets as described above to accommodate the eye before the long pulse is initiated. In some embodiments, long pulse measurement beam is much longer that 500 ms and comprises a continuous measurement beam. In some embodiments, a standard video frame rate of about 33 ms per frame can be used, such that about 15 video frames can be acquired during the long pulse measurement beam. Work in relation with embodiments of the present invention indicates that long pulse measurement beams, while suitable for some embodiments, may permit the eye to move while the beam is pulsed and may be somewhat limited by the safety threshold.

FIGS. 6C and 6D show a short pulse measurement light beam 260 and camera timing signal 262, according to embodiments of the present invention. The amplitude of the short pulse 260 can exceed the amplitude of the long pulse while keeping the average power within the safety threshold 254. Camera timing signal 262 can open a camera shutter in synchronization with the short measurement light beam pulse. The source may be pulsed multiple times in series to make multiple synchronized measurements.

The duty cycle of the source can be designed by considering the time for a single capture and motion of the eye. The combination of intensity of the source and duty cycle of the source can be determined so as to optimize measurement of the eye and stay far below safety threshold limits. In some embodiments, a short measurement light beam pulse comprises a duration that is no longer than a video frame of about 33 ms. In some embodiments, an intensity of short pulse 260 can exceed long pulse safety threshold 254 by a factor of at least 5, and in some embodiments the short pulse threshold can exceed long pulse threshold 254 by a factor of at least 10. For example, when the short pulse has a 10 ms on duration and a 90 ms off time duration, the cycle period comprises 100 ms duration; the duty cycle is 0.1, or 10%, and the pulse amplitude may be 10 times the long pulse amplitude.

The amount by which an intensity of short pulse 260 can exceed long pulse safety threshold 254 can depend on the duration of the short pulse, the wavelength of light and applicable standards, for example ANSI and European standards that may apply. In some embodiments comprising a measurement beam with a near infrared wavelength from about 700 nm to 1.5 um, for example about 780 nm, the maximum allowable power for a 10 second exposure may be at least about 500 microwatts. In some embodiments using visible wavelengths, for example from about 400 to 700 nm, the maximum allowable safe power may be lower than for near infrared wavelengths.

Work in relation with embodiments of the present invention indicates that the safety levels proposed by ANSI and European standards may exceed levels that interfere with fixation for measurement beams that comprises visible and near infrared light wavelengths. In some embodiments, the measurement beam may comprise pulses that are well below the safety threshold, such that the measurement light beam has minimal interference on fixation, and ideally no interference on fixation. For example with near infrared wavelength of about 780 nm, the measurement beam may be perceptible to some patients, such that it may be desirable to pulse the near infrared measurement beam so as to avoid interference with the fixation target. In specific embodiments, a 10 second exposure level for a 780 nm measurement beam can be set to about 50 microwatts, well under the safety limits, so as to avoid interference with target fixation and/or relaxation of accommodation. In embodiments with single near infrared pulses within each cycle of 3.3, 9.9 and 16.5 ms and a repetition period of 33 ms, the maximum allowable short pulse intensities may comprise 500 microwatt, 166 microwatt and 100 microwatt intensity pulses so as to avoid interference with fixation and/or accommodation. In some embodiments, the maximum intensity for five 1 ms pulses over five video frames may be greater than the maximum intensity for a single pulse of 5 ms, such that the longer pulse duration, for example 5 ms, may provide a conservative safety threshold for the sequence of shorter pulses, for example a sequence of five 1 ms pulses. In some embodiments, the duty cycle of the short measurement light beam pulse is determined by the duration of the pulse and the video frame rate of sequential video frames. Thus, for 1, 5 and 10 ms pulses and a video frame rate of about 33 ms, the duty cycles are 3, 15 and 30 percent, respectively. Although specific embodiments are described above with reference to near infrared light beams, similar pulsing and duty cycles can be used with embodiments comprising measurement light beams in the visible portion of the electromagnetic spectrum from about 400 to 700 nm, so as to avoid interference of the measurement light beam with target fixation and/or relaxation of accommodation.

Figure 7:
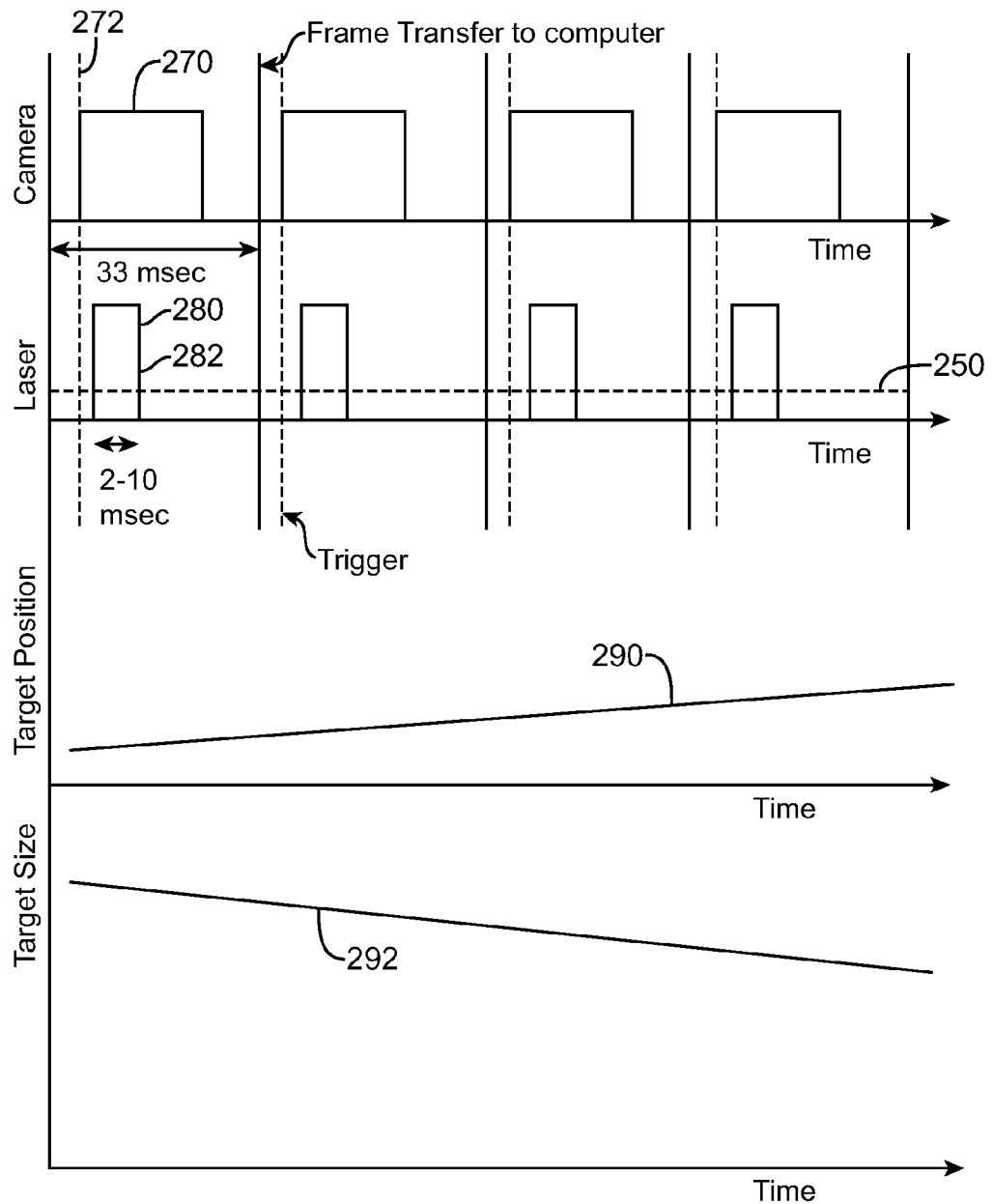
FIG. 7 shows a timing diagram for a camera shutter signal, a pulsed measurement beam signal, target position signal and target size signal, according to embodiments of the present invention.

FIG. 7 shows a timing diagram for a camera shutter signal 270, a pulsed measurement beam signal 280, a target position signal 290 and a target size signal 292, according to embodiments of the present invention. In some embodiments, a common timing signal is provided such that camera shutter signal 270, pulsed measurement beam signal 280, target position signal 290 and target size signal 292 are synchronized in response to the common timing signal. Camera shutter signal 270 controls the camera shutter. A trigger 272 opens the camera shutter. Pulsed measurement beam signal 280 triggers a short duration measurement beam pulse 282. Short duration measurement beam pulse 282 are often no more than about 100 ms and can be from about 1 ms to 100 ms, and from about 2 to 10 ms, for example 5 ms. Short duration beam pulse 282 can be a initiated after trigger 272, for example 1 ms after trigger 272, such that the shutter is fully open when the measurement beam pulse occurs. Target position signal 290 controls the position of the target, for example a lateral transverse position of the target. In some embodiments, target position signal 290 controls horizontal and vertical translational positions of the target on the display and also controls rotational orientation of the target on the display. Target size signal 292 controls a size of the target on the display. In some embodiments, the target position, size and rotation controls signals may each comprise discrete stepwise digital signals with suitable resolution, for example 8 bit resolution or higher. In some embodiments, the target moves to a desired position, rotation and magnification before the measurement light beam is pulsed, as the measurement beam can be visible to the patient and may distract the patient from the target. In some embodiments, the pupil measurement camera has a shutter control signal that is synchronized with the measurement light beam such that the position of the eye can be correlated with the camera to determine whether the patient's eye has followed the target. In some embodiments, the target may be moved asynchronously and the measurement beam pulsed so as to measure the eye with a stroboscopic series of measurements.

In some embodiments, the response of the patient's eye can be tested in many ways. The subject can be requested to visually follow the moving target while the device tracks the eye. The instrument computer knows the target's exact dioptric focus, location and motion dynamics. The subject may be requested to evaluate the target by giving a very brief description of the moving object. The computer can calculate the dynamics of the eye's position and correlate it to the position of the object in the scene. In response to this analysis, the computer can determine if the subject is focusing on the moving target object. The computer also may compute the focus error of the eye, and compare the focus error with target object's vergence and/or dioptric focus, and drive the dynamics of accommodation, for example the focus error as a function of time. By this analysis, the computer can determine the subject's effectiveness of accommodation relaxation over a range of target vergence. While the target is placed at optical infinity, accommodation may relax to the far point of the eye with myopic and emmetropic patients. While the target is place a nearer vergence, the steady state accommodation may correspond to that vergence. In some embodiments, the instrument can control the accommodation of the eye under test and perform many desired measurements of the eye in response to the vergence of the accommodative stimulus. Thus, the accommodation and/or pupil dynamics corresponding to the target object's vergence may also be obtained. The range of accommodation may also be determined by presenting targets at different target vergences over a range of vergences. Embodiments may also increase or decrease the visual size of the moving object as seen by the patient to evaluate visual acuity of the patient.

Figure 8:
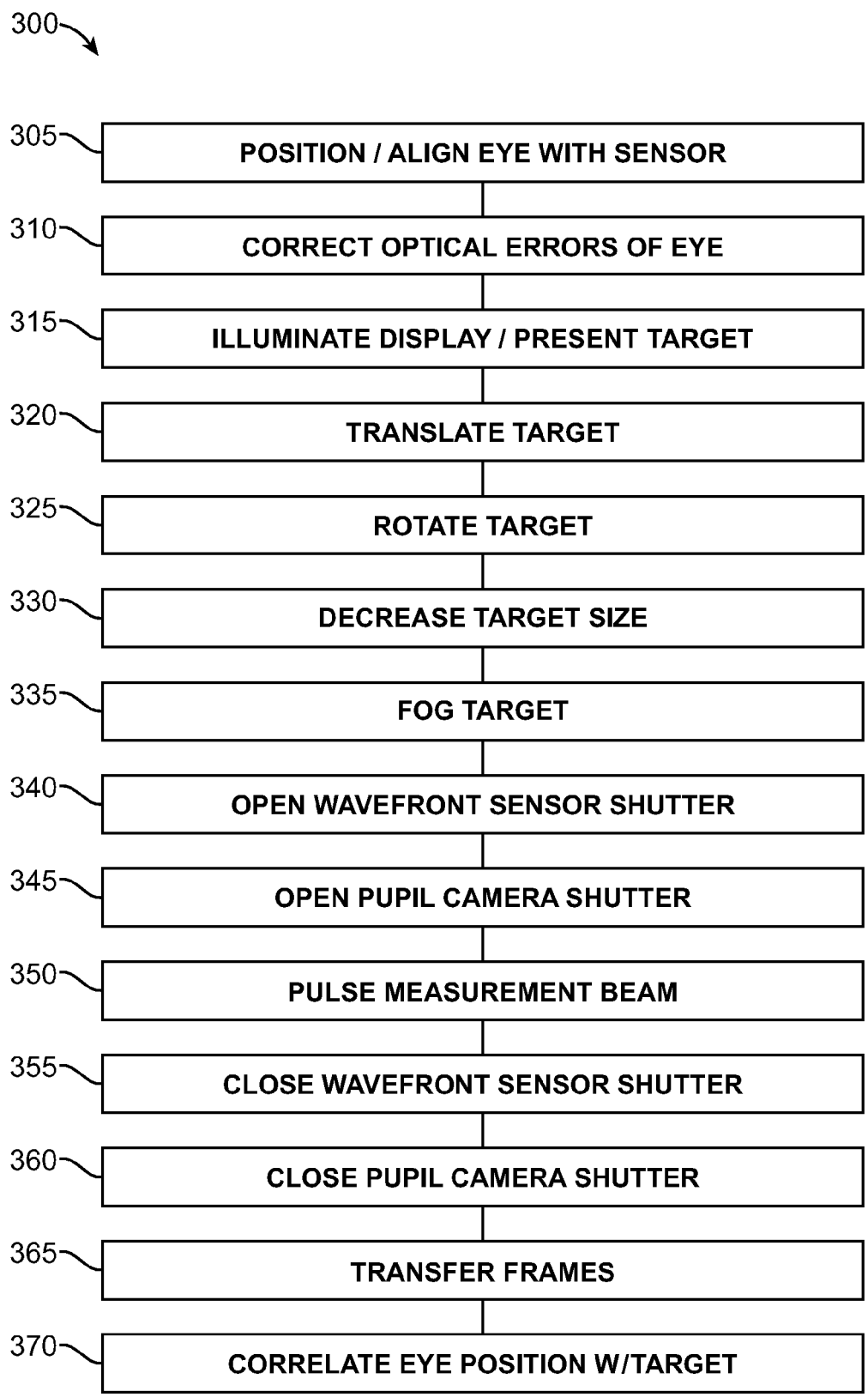
FIG. 8 shows a method of measuring optical properties of an eye, according to embodiments of the present invention.

FIG. 8 shows a method 300 of measuring optical properties of an eye, according to embodiments of the present invention. A step 305 positions and/or aligns the eye with the measurement system to measure the eye. A step 310 corrects for optical errors of the eye with optics of the wavefront system. A step 315 illuminates a display and presents a target to the patient. A step 320 translates the target transverse to the optical axis to relax an accommodation of the eye. A step 325 rotates the target. A step 330 decreases the size of the target such that the patient perceives the target moving away from the patient. A step 335 fogs the target such that the target is perceived by the eye as farther from the patient so as to relax an accommodation of the patient. In some embodiments, step 320, step 325, step 330 and step 335 occur simultaneously. A step 340 opens a wavefront sensor camera shutter. A step 345 opens a pupil camera shutter. A step 350 pulses a short duration measurement light beam for a short duration. A step 355 closes the wavefront sensor camera shutter. A step 360 closes the pupil camera shutter. A step 365 transfers the frames from the wavefront sensor and the pupil camera sensor to the computer. A step 370 correlates eye position with target position. Step 305 to step 370 can be repeated such that several measurements are taken. In some embodiments, steps 305 to 370 can be automated, and the aberrations of the eye may not be corrected with adaptive optics.

It should be appreciated that the specific steps illustrated in FIG. 8 provide a particular method of measuring an eye, according to an embodiment of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. An optical device to diagnose an eye of a patient, the device comprising: a display with a visible target visible to a patient; an optical system to project the visible target along an optical path from the display to the patient, the optical system comprising a lens to provide positive optical power when the visible target is fogged and wherein the display is coupled to the optical system to move the visible target with a movement transverse to the optical path when the visible target is fogged; a sensor coupled to the optical system to measure optical aberrations of the eye; and a processor coupled to the display, the optical system and the sensor, the processor having a computer readable memory with instructions embodied thereon to fog the visible target with the optical system, to decrease a size of the visible target on the display when the visible target is fogged, to move the visible target on the display with the movement transverse to the optical path when the target is fogged, and to measure the optical aberration of the eye with the sensor in response to the decreased size and movement of the visible target transverse to the optical path, wherein the processor has instructions to display a stationary scene having a stationary visible image of an object and to move the visible target along the stationary scene transverse to the optical path when the stationary image is displayed.

2. The optical device of claim 1 wherein the movement of the visible target transverse to the optical path comprises at least one of a translation or a rotation of the target.

3. The optical device of claim 1 wherein the display comprises a microdisplay with pixel elements.

4. The optical device of claim 1 wherein the display comprises a computer addressable display with pixel elements that move the target across the display.

5. The optical device of claim 1 wherein the display comprises at least one of an organic light emitting diode microdisplay, a liquid crystal microdisplay, a liquid crystal on silicon microdisplay, or a MEMS microdisplay.

6. The optical device of claim 1 wherein the processor is configured with the instructions to rotate virtually a visible target object on the display.

7. The optical device of claim 1 wherein the processor is configured with the instructions to correlate a position of the visible target transverse to the optical path with a position of the eye.

8. The optical device of claim 1 wherein the processor is configured with the instructions to adjust a vergence of the visible target with the optical system and measure a range of accommodation of the eye in response to the vergence of the visible target.

9. The optical device of claim 1 further comprising a sensor to measure a position of the eye as the visible target moves transverse to the optical path.

10. A method of diagnosing an eye with a sensor, the method comprising: presenting a visible target on a display visible to a patient; projecting the visible target along an optical path from the display to the patient such that the patient sees the visible target; fogging the visible target with positive optical power such that the visible target appears blurred to the patient; moving the visible target transverse to the optical path, wherein the display comprises a stationary scene having a stationary visible image of an object and wherein the target moves along the stationary scene transverse to the optical path when the stationary visible image is shown on the display; decreasing a size of the visible target when the visible target is fogged and moved transverse to the optical path and wherein an accommodation of the eye relaxes when the visible target moves transverse to the optical path; and measuring optical aberrations the eye with the sensor when the accommodation is relaxed in response to the visible target moving transverse to the optical path.

11. The method of claim 10 wherein the target is moved transverse to the optical path with at least one of a translation or a rotation.

12. The optical device of claim 1 wherein the processor has instructions to display a scene comprising the visible target and a visible image of an object and wherein processor has instructions to move the visible target along the scene toward the visible image with a translation transverse to the optical path to relax the eye.

13. The optical device of claim 12 wherein the transverse movement of the visible target along the scene comprises the translation of the visible target and a rotation of the visible target.

14. The optical device of claim 12 wherein the display comprises a computer addressable display with pixel elements that move the visible target along the scene of the display.

15. The optical device of claim 1 wherein the processor has instructions to move the visible target along the scene away from the visible image with a translation transverse to the optical path to relax the eye.

16. The optical device of claim 15 wherein the transverse movement of the visible target along the scene comprises the translation of the visible target and a rotation of the visible target.

17. The optical device of claim 15 wherein the display comprises a computer addressable display with pixel elements that move the visible target along the scene of the display.

18. The method of claim 10 wherein the visible target moves along the scene toward the visible image with a translation transverse to the optical path.

19. The method of claim 18 wherein the transverse movement of the visible target along the scene comprises the translation of the visible target and a rotation of the visible target.

20. The method of claim 18 wherein the object comprises a stationary object when the visible target moves with the translation transverse to the optical path.

21. The method of claim 10 wherein the visible target moves along the scene away from the visible image with a translation transverse to the optical path.

22. The method of claim 21 wherein the transverse movement of the visible target along the scene comprises the translation of the visible target and a rotation of the visible target.

23. The method of claim 21 wherein the object comprises a stationary object when the visible target moves with the translation transverse to the optical path.

* * * * *